United States Patent [19]

Jacobson

[11] 4,293,567
[45] Oct. 6, 1981

[54] ANTI-FEEDANT FOR BOLL WEEVILS

[75] Inventor: Martin Jacobson, Silver Spring, Md.

[73] Assignee: The United States of America as represented by the Secretary of Agriculture, Washington, D.C.

[21] Appl. No.: 140,911

[22] Filed: Apr. 16, 1980

[51] Int. Cl.$^3$ .............................................. A01N 37/06
[52] U.S. Cl. ............................. 424/312; 260/410.9 R; 260/413; 424/DIG. 10
[58] Field of Search ....................... 424/312, DIG. 10

[56] References Cited

PUBLICATIONS

Hardee et al., J. Economic Entomology 59, 1267–1270 (1960).
Crombie et al., J. Chem. Soc., 1632–1646 (1957).
Jacobson et al., Talk Presented at National Meeting of the Entomological Society of America, Denver, Col., Nov. 25–29, 1979.

Primary Examiner—Allen J. Robinson
Attorney, Agent, or Firm—M. Howard Silverstein; William E. Scott; David G. McConnell

[57] ABSTRACT

An anti-feedant is applied to cotton plants to deter boll weevils from puncturing the cotton bolls. The anti-feedant is the methyl ester of α-eleostearic acid. The material may be applied by spraying in dilute solution. The ester is obtained in high yield by saponification of tung oil followed by solvent extraction and crystallization of the acid, and subsequent esterification with methyl alcohol.

3 Claims, No Drawings

ANTI-FEEDANT FOR BOLL WEEVILS

BACKGROUND OF THE INVENTION

1. Field of the Invention

This invention relates to a boll weevil feeding deterrent, to a method of treating cotton therewith, and to a method of obtaining a boll weevil feeding deterrent. A boll weevil feeding deterrent is a material which, when applied to cotton, deters the attack of the boll weevil upon the cotton.

2. Description of the Art

Although it is known that tung oil contains a feeding deterrent for the boll weevil, the identity of the deterrent has not heretofore been discovered. Currently, insecticides are used to control boll weevils and prevent extensive damage to cotton.

SUMMARY OF THE INVENTION

It is an object of the present invention to provide an effective boll weevil feeding deterrent as an alternative or supplement to the use of insecticides to control boll weevils in the growing of cotton.

It is a further object of the invention to provide a method of treating cotton with a boll weevil feeding deterrent.

It is still another object of the present invention to provide a method of obtaining a boll weevil anti-feedant precursor from a naturally occurring material.

In general, according to this invention, the above and other objects which will be apparent to those of ordinary skill in the art are accomplished by applying an effective boll weevil deterrent amount of methyl α-eleostearate to growing cotton. The ester is preferably obtained by esterification of the acid after recovery of the acid from tung oil. The acid is preferably obtained from tung oil by a saponification process which includes the following steps: saponifying tung oil in an organic solvent with a saponification agent, acidifying the saponified tung oil reaction mixture with aqueous acid solution, admixing the resulting acidified product with a further organic solvent for α-eleostearic acid to form an aqueous phase and an organic solvent phase containing α-eleostearic acid, separating the aqueous and organic phases, drying the organic phase, evaporating the further organic solvent from the dried organic phase to form a residue, dissolving the residue in a crystallization solvent, cooling the crystallization solvent to form a crystalline product comprising α-eleostearic acid, and separating the crystalline product and crystallization solvent.

DESCRIPTION OF THE INVENTION

Methyl α-eleostearate (methyl Z,E,E-9,11,13-octadecatrienoate) has the structural formula:

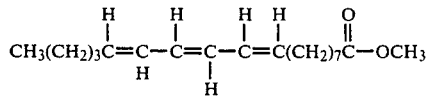

The compound is conveniently prepared from α-eleostearic acid by refluxing in a nitrogen atmosphere for 2 hours a solution of 5 grams of α-eleostearic acid in 50 ml. of methyl alcohol containing one drop of concentrated sulfuric acid (catalyst), removing the solvent by evaporation at 15 mm pressure and 30° C., pouring the residue into several volumes of water, and extracting the solution with several portions of ether. The combined ether solution is dried over sodium sulfate (anhydrous) and freed of ether by evaporation at 15 mm pressure. The product may be distilled before use, but this is not ordinarily necessary.

The methyl α-eleostearate obtained in this manner is a clear, colorless to pale yellow, oily liquid with little or no odor, having the following physical properties:

Boiling Point: 160°–165° C. (1.0 mm); 210°–214° C. (12 mm)

Refractive Index: $n_D^{25}$ 1.5000±0.0025

Density: 0.867±0.007 g/ml at 25° C.

The compound thus prepared contains at least about 98% by weight of methyl α-eleostearate and not more than about 1.5% by weight of methyl β-eleostearate (all-trans isomer). Methyl α-eleostearate is easily analyzed by gas liquid chromatography.

The effect of the application of methyl α-eleostearate on growing cotton is illustrated in the following example:

EXAMPLE

A one percent (1%) solution of several candidate treating agents in a suitable solvent is applied to an unpunctured, debracted bud of a greenhouse-grown cotton plant by momentarily dipping the bud into the solution. In this example, acetone was the solvent of choice. Ten one or two day old adult boll weevils, unfed from time of emergence or starved for 24 hours, are placed in a petri dish with one treated bud and one control bud that is first dipped in the same solvent (acetone) only and held for four hours. The number of feeding punctures per bud is counted under a dissecting microscope.

| Feeding Deterrent | Punctures per bud | |
|---|---|---|
| | Control | Treated |
| α-eleostearic acid | 60 | 27 |
| β-eleostearic acid | 43 | 34 |
| methyl α-eleostearate | 60 | 9 |
| ethyl α-eleostearate | 39 | 35 |

It is readily observed that methyl α-eleostearate is dramatically better as a feeding deterrent than the other closely related materials tested.

Methyl α-eleostearate for this test is obtained from α-eleostearic acid as indicated above. Ethyl α-eleostearate is obtained in a similar manner, but using ethyl alcohol instead of methyl alcohol. The alpha and beta eleostearic acids are obtained from tung oil which is obtained from tung nuts.

The tung tree is a native of China, where the oil expressed from the fruit (called tung oil or Chinese wood oil) was used for centuries as a water proofing agent. Tung trees were planted in the United States and the nuts were harvested on a commercial scale for making Tung oil for use in the production of varnishes and resins. Millions of trees were grown on tung plantations in the southern states. With the advent of less expensive synthetic materials, the need for tung oil greatly decreased. Consequently, there are relatively few tung trees remaining in the United States. In the United States tung oil is used now for formulating burn remedies and the oil-free meal is used as a fertilizer.

Tung oil is obtained by solvent extraction of tung fruits. For example, tung fruits (4 kilograms) are extracted with pentane in 5-liter Soxhlet extractors to yield a total of 1.2 kilograms of yellow, odorless oil.

The α-eleostearic acid is prepared from the tung oil as follows. One hundred and thirty-four grams of tung oil is mixed with 500 ml ethanol, 54 grams of potassium hydroxide, brought to a boil, and refluxed for four hours under a nitrogen atmosphere. After cooling in an ice bath, a 10% aqueous sulfuric acid solution is added in an amount sufficient to render the system acidic, with the α-eleostearic acid being present in an oily layer on top of an aqueous layer. Ether, in an amount approximately equal to the volume of the oily layer, is added to the system and the vessel is shaken to dissolve the oily acid in the ether. The ether layer which settles out is then separated and dried with sodium sulfate. The ether is evaporated and the acid residue is taken up in acetone and crystallized at about −20° C. The crystalline α-eleostearic acid has a melting point of 48° C. The yield from 134 grams of tung oil is 75 grams of acid.

It will be seen that the yield of α-eleostearic acid obtained in this method is extremely high: 56% by weight based on the tung oil. This compares very favorably with the yield obtained by other techniques which have been reported in the art such as that reported in J. Chem. Soc. (1957) pp. 1632–1646 at p. 1641, in which the yield of α-eleostearic acid was only about 36% by weight and the product had a melting point of 47°–48° C. In that method, the acidified material was washed twice with hot distilled water. After one hour at 0° C., the solid was filtered off and recrystallized four times from ethanol and twice from pentane.

In the method of obtaining α-eleostearic acid from tung oil in the present invention, the solvent used for the saponification of the tung oil is one which will dissolve the tung oil, the saponification agent, and the reaction products. Alcohols are preferred, preferably those having up to five carbon atoms. The saponification agent may be potassium hydroxide, sodium hydroxide, calcium hydroxide, or the like. It is preferable to exclude oxygen in order to minimize the formation of β-eleostearic acid. Accordingly, nitrogen or other inert gas atmosphere is preferably employed during saponification and may also be employed during other stages of the process, particularly where temperature is elevated since heat also induces the formation of β-eleostearic acid. Other non-interfering acids, such as hydrochloric, may be used in lieu of sulfuric. Of course one would avoid a reactive acid such as nitric. Enough acid is added to render the system acidic; excess acid is not harmful. The α-eleostearic acid is then dissolved out of the system by any good, non-interfering, solvent for the acid, such as ether. Other solvents, such as hexane and pentane may also be used, but ether is preferred for its high solvent action. The solvent layer is separated in any convenient manner and dried with any non-interfering anhydrous drying agent such as sodium sulfate, potassium sulfate, magnesium sulfate or the like. Interfering drying agents, such as calcium chloride (which would react with any dilute alcohol present) are not suitable. The ether is evaporated, preferably by reducing pressure at a relatively low temperature to avoid formation of the beta acid. The alpha acid residue is taken up with a solvent from which it crystallizes at low temperature. Acetone is preferred for this purpose.

As mentioned above, the process of treating tung oil in accordance with the invention achieves the alpha eleostearic acid in high yield. The acid is readily esterified with menthanol to form the methyl ester in quantitative yield. Accordingly, the yield of the highly active boll weevil antifeedant (methyl α-eleosterate) is extremely high. As indicated above, the methyl α-eleostearate is applied to growing cotton in any suitable manner to deter boll weevils from feeding on the cotton. It is preferred to apply the agent by spraying and more preferably by means of aqueous spray from conventional commercial spraying equipment. The agent is preferably applied in dilute solution, for exmaple 1% by weight, in an appropriate carrier. For large commercial operations, the carrier is preferably water. Methyl α-eleostearate is not soluble in water, of course, and the term "solution" as used herein to describe the cotton treatment composition is used in a general sense to include dispersions, emulsions, etc., and not in the limited technical sense of a true solution. Where the carrier is water, a surfactant is preferably used to form an emulsion. While it is preferred to form a stable emulsion, it is also appropriate to utilize agitation to maintain a dispersion of the agent in the carrier prior to its application. The amount of treatment composition to be applied to the cotton, its frequency of application, and the concentration of treating agent in the composition can vary widely and will in large measure be dependent upon the size of the cotton field, the nature of the application equipment on hand, the relative costs of labor and application equipment, and the like. In general, it is convenient to spray the composition, in the form of a dilute aqueous solution of the agent, in amounts conventionally used to spray similar dilute solutions of insecticides on cotton plants.

The anti-feedant is conveniently provided in a concentrated solution for dilution prior to application. A typical application would be 1/10 gallon per four acres. This is readily accomplished by providing a 10% (by volume) solution or suspension of the material which is diluted, prior to application, with water in an amount sufficient for thorough coverage.

I claim:

1. A method of deterring boll weevils from feeding on growing cotton plants comprising applying methyl α-eleostearate to growing cotton plants in an amount sufficient to deter boll weevils from feeding thereon.

2. A method according to claim 1 wherein the methyl α-eleostearate is applied to the growing cotton plants dispersed in a liquid carrier.

3. A method according to claim 2 wherein said liquid carrier comprises water.

* * * * *